Figure 1:
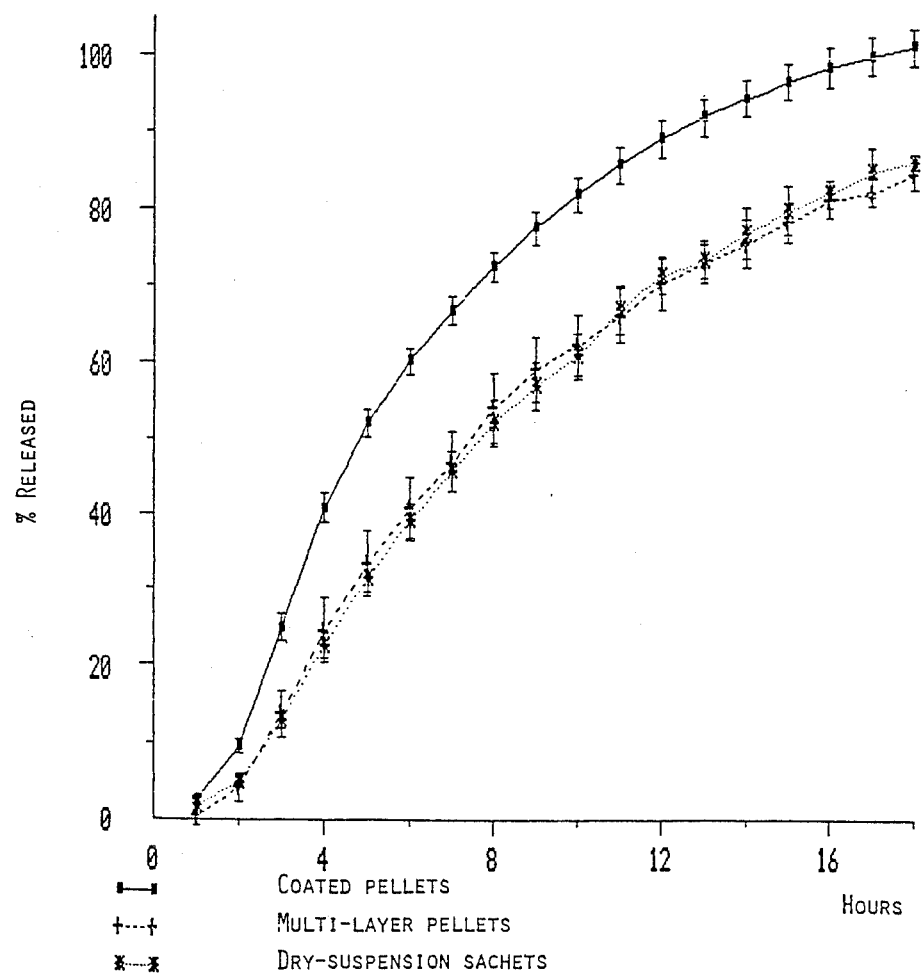

United States Patent [19]

Ventouras

[11] Patent Number: 4,882,169
[45] Date of Patent: Nov. 21, 1989

[54] SWELLABLE PELLETS
[75] Inventor: Kimon Ventouras, Le Lignon, Switzerland
[73] Assignee: Zyma Sa, Nyon, Switzerland
[21] Appl. No.: 151,502
[22] Filed: Feb. 2, 1988
[30] Foreign Application Priority Data
Feb. 3, 1987 [GB] United Kingdom ................ 8702411
[51] Int. Cl.$^4$ .............................................. A61K 9/16
[52] U.S. Cl. ..................... 424/493; 424/494; 424/495; 424/496; 424/497; 424/451
[58] Field of Search ............... 424/496, 493, 494, 497, 424/443, 451; 206/535, 540

[56] References Cited
U.S. PATENT DOCUMENTS
3,946,110  3/1976  Hill ....................................... 424/230
4,341,759  7/1982  Bogentoft et al. .............. 424/490 X
4,721,619  1/1988  Panoz et al. ......................... 424/459

FOREIGN PATENT DOCUMENTS
0052076   5/1982   European Pat. Off. .
0076428   4/1983   European Pat. Off. .
0153104   8/1985   European Pat. Off. .
0181564   5/1986   European Pat. Off. .
122938    5/1962   New Zealand .
129252    8/1964   New Zealand .
146117    4/1970   New Zealand .
172921    7/1975   New Zealand .
170977    9/1975   New Zealand .
86/04817  8/1986   PCT Int'l Appl. .
86/06626 11/1986   PCT Int'l Appl. .
2086725   5/1982   United Kingdom .
2103486   2/1983   United Kingdom ................ 424/490
2166651   5/1986   United Kingdom .

Primary Examiner—Thurman K. Page
Attorney, Agent, or Firm—Wenderoth, Lind & Ponack

[57] ABSTRACT

Pellets which can be used in liquid oral formulations of drugs are presented. They comprise (a) a core, containing microparticles of at least one pharmaceutically active substance, (b) optionally one or more coating layer(s) and (c) a swellable outer layer. They are manufactured by methods known per se.

14 Claims, 1 Drawing Sheet

IN VITRO RELEASE OF METHYL-XANTHINES FROM COATED PELLETS, MULTI-LAYER SWELLABLE PELLETS AND DRY SUSPENSION OF MULTI-LAYER SWELLABLE PELLETS

SWELLABLE PELLETS

The present invention relates to the oral administration of pharmaceutically active substances. Especially, it is concerned with the problem of formulating pellets, preferably coated pellets, e.g. such with controlled release or taste masking properties or enterically coated ones, as liquids. Thus, the invention relates to improved pellets, advantageously multi-layer pellets, which contain at least one pharmaceutically active substance and a swellable outer layer. In contact with water, the outer layer of the pellets swells and rapidly becomes jellified. Thus the suspension formed can be swallowed easily by any person who is in need of the pharmaceutically active substance(s) without having any unpleasant hoarse feeling in the mouth.

This route of administration of pharmaceutically active substances is particularly advantageous, when a relatively large single dose must be applied orally, since a tablet or another shaped form, e.g. a capsule, would be too voluminous for oral intake. Also in cases where no particularly large single dose must be applied, the route of administration described above can be advantageous, because it is more convenient especially for children and elderly people, and other people too, who often have troubles swallowing medicines in solid form, such as tablets or other shaped forms. Furthermore, there are certain drugs, where multiple unit dosage forms are particularly advantageous to overcome a local irritation of the gastrointestinal tract after peroral administration, e.g. non-steroidal antiinflammatory drugs, such as ibuprofen, or other drugs, e.g. potassium chloride or sodium fluoride.

Tablets which rapidly disintegrate in water and contain coated pellets are known in the art, e.g. from EP-A-52 076 or WO-A-86/04 817. However, these tablets suffer from some disadvantages: After disintegration, they form a dispersion containing the isolated - mostly coated - microparticles. Even in those cases where the microparticles used are of small size - e.g. of 0.3 to 0.6 mm diameter -, when swallowed, they are perceived as individual grains in the mouth in an unpleasant manner and may be caught on the spaces between the teeth. Generally spoken, the dispersion prepared from such tablets produces a certain feeling of hoarseness in the mouth.

Furthermore, often liquid foods, e.g. apple sauce or marmalade, are needed to administer the tablets known in the art. The use of the latter has the following disadvantages: (1) The person in need of the drug always has to take in food simultaneously when swallowing a formulation of the invention. But food intake can often be completely undesired in such situations, e.g. for reason of avoiding increase of weight. (2) Drug absorption may be influenced by the food taken in simultaneously in an undesired manner.

Another approach to obtain a liquid formulation containing coated pellets, especially for use as a geriatric and pediatric galenic form, is described in GB-A-2 166 651: So-called "pharmasomes" are disclosed which are polymeric mini-matrix systems with particles sizing from 0.0001–0.125 mm or less. When put into water, a suspension is formed which - when swallowed - is stated to be void of any unpleasant feeling in the mouth. That the problem concerned is not a simple one, can be seen from the following citation of this reference (page 1, line 9): "Sustained release pellets cannot be readily formulated as liquids".

The disadvantages of the formulation described in GB-A-2 166 651 are e.g. that (1) employing an expensive new technology is necessary to produce the - unusually small - particles needed and (2) new polymers are used for which expensive toxicology studies have to be performed before they may be applied in pharmaceutical formulations for humans.

It is therefore the aim of the present invention to provide pellets, which can be manufactured solely from conventional materials known in the art, e.g. from particles of up to e.g. 3.0 mm diameter, which form a perfectly homogeneous dispersion when put into water, and in which, when taken up by mouth and swallowed, no individual grains can be perceived any more. Moreover, this goal is to be achieved without the need of any liquid foods. Finally, the pellets of the invention are to be manufactured without the use of organic solvents, because that is highly desirable for a modern, ecologically orientated pharmaceutical production.

Thus, the present invention relates to pellets comprising (a) a core, containing microparticles of at least one pharmaceutically active substance, (b) optionally one or more coating layer(s) and (c) a swellable outer layer.

The microparticles of the pharmaceutically active substances used are e.g. granules, crystals or pellets of said active substances. Their size is e.g. 0.2–3.0 mm diameter, preferably 0.3–1.5 mm and especially 0.6–1.2 mm diameter.

The core (a) optionally contains usual excipients, e.g. binders, plasticizers, glidants, absorbing substances and/or swellable materials as defined below.

As pharmaceutically active substances used in the pellets of the invention come into consideration all those which are suitable for peroral administration. This applies for example for (a) potassium chloride administered e.g. in the treatment of hypokaliaemia, (b) lithium salts administered e.g. in psychotherapy, (c) non-steroidal antiinflammatory drugs, e.g. ibuprofen or naproxen, (d) calcium salts e.g. in therapy of hypocalcemic states or for calcium supplementation, (e) sodium fluoride e.g. in the treatment of osteoporosis, (f) pridinol, or a salt thereof, e.g. as a muscle relaxant, (g) dimethindene, or a salt thereof, e.g. as an antihistaminicum, (h) methyl-xanthines, e.g. proxyphylline, diprophylline and/or theophylline, e.g. as bronchodilators, (i) a mixture of 0-$\beta$-hydroxyethyl-rutosides (Venoruton ®) e.g. in the treatment of venous diseases, (j) antitussive drugs, e.g. butamirate of a salt thereof, such as butamirate citrate, codeine or a derivate thereof, noscapine, or dextromethorphan or a salt thereof, such as dextromethorphan hydrobromide, (k) antipyretics, e.g. acetaminophen, (l) vitamines and multivitamines preparations, (m) cardiovascular and vascular drugs, such as all the betablockers known in the art, or e.g. 1-0-ethyl-3-0-propyl-5,6-di-0-(4-chlorobenzyl)-D-glucofuranoside, (n) drugs especially used against elderlys' or childrens' diseases (geriatric or pediatric drugs), e.g. pyrisuccideanol or a salt thereof, such as pyrisuccideanol dimaleate, ticlopidine, dipyridamole or diazepam, (o) drugs useful to balance the hydroelectrolytes e.g. for the treatment of diarrhoea, e.g. sodium or potassium salts, (p) antibiotic drugs, e.g. erythromycin, or a salt thereof, doxycycline, or a salt thereof, (q) nootropica, e.g. piracetam, (r) anthelmintica, e.g. mebendazole, or (s) histamine $H_2$ receptor antagonists, e.g. cimetidine or ranitidine. All the salts mentioned above must of course be pharmaceutically acceptable so as to be used in the pellets of the invention.

Preferably, the core (a) is surrounded by one or more, especially one, coating layer(s) (b). Such coating layer(s) may consist of any material which is known in the art to be suitable for the intended purpose, or mixtures of different materials, e.g. polymeric materials. For manufacturing such coatings, the coating material is dissolved in organic solvents or dispersed in water as a latex and then sprayed on the cores. The intended purpose of the coating may be e.g. either any kind of controlled release of a certain pharmaceutically active compound as well-known in the art, or masking of any undesired, e.g. bitter, taste of such a compound. The coating materials can be e.g. water-insoluble or water-soluble polymers, or mixtures thereof. Moreover, the coating may contain usual auxiliaries, e.g. plasticizers and/or glidants.

However, the coating layer(s) (b) is (are) an optional measure, and also cores (a) only coated by the swellable outer layer (c) are an embodiment of the present invention.

The swellable outer layer (c) may contain any swellable material which is pharmaceutically acceptable. It may be e.g. a naturally occurring or a chemically obtained swellable polymer. Examples for useful swellable materials are xanthan gum and derivatives thereof; guar gum and derivatives thereof, e.g. hydroxypropyl guar or carboxymethylhydroxypropyl guar (e.g. Jaguar ® gums); alginates, polysaccharides, e.g. dextran; pectins; cellulose derivatives, such as sodium or calcium carboxymethylcellulose, hydroxypropylcellulose or hydroxypropylmethylcellulose (e.g. Methocel E4M Prem., Methocel K15M Prem. or, preferably, Methocel K100M Prem., all supplied by Dow Chem., Midland, Mich., USA); polyvinyl alcohol; or pregelatinized starches. Also swellable acrylic polymers, such as the polymers and copolymers mentioned in U.S. Pat. No. 4,277,582, come into consideration as the swellable material of the outer layer (c). The preferred material for the swellable outer layer (c) is guar gum.

The swellable outer layer (c) optionally contains usual auxiliaries, e.g. binders. As binders, all polymers with high binding properties can be used, either in dispersion in organic solvents or preferably in aqueous medium. Typical examples of binders are shellac, ethylcellulose, polyvinylpyrrolidone, gelatine, hydroxypropylcellulose or neutral acrylic polymers, such as poly(H or meth)-acrylic acid (methyl or ethyl) ester, and mixtures thereof. Preferred as binder is a 1:1 mixture of 7 % w/w hydroxypropylcellulose in water, e.g. Klucel ®-LF, and an ethyl acrylate/methyl methacrylate copolymer, such as Eudragit ® NE-30-D.

The pellets of the invention in addition may contain e.g. flavourings and/or sweeteners, preferably in the swellable outer layer (c).

The pellets of the invention, alone or in admixture with conventional excipients, can be used to prepare pharmaceutical preparations for oral administration. For example, they can be formulated as a dry suspension containing the pellets of the invention and optionally appropriate excipients. Excipients suitable for that purpose are e.g. granules of a swellable material as defined above which optionally contain flavourings and/or sweeteners. Such a dry suspension can e.g. be packed into sachets for reconstitution with water for single dose oral administration.

When put into water, e.g. water in a spoon or a cup of water, the pharmaceutical preparations of the invention are rapidly dispersed so as to generate a viscous, homogenous suspension which can be swallowed easily without any unpleasant hoarse feeling in the mouth. As can be seen from the definitions above, even microparticles of big size - e.g. up to 3 mm diameter - can be used for this purpose due to the unique composition of the pellets of the invention.

Administering pharmaceutically active compounds as a viscous, homogeneous suspension - like jam or jelly - e.g. in a spoon represents an advantageous, new approach for orally administering medicine, especially to children.

The pellets according to the invention are manufactured in a manner known per se. The materials forming the core (a) are intimately mixed and then processed to cores of a suitable size by conventional methods. Optionally, the cores obtained are coated by one or more coating layers(s) (b) in a manner known per se. The swellable material is fixed on the pellets obtained as the outer layer e.g. in a rotating high speed mixer allowing simultaneous drying e.g. with the aid of a binder, which preferably is suspended in water. The binder suspension is e.g. continuously sprayed on the pellets rotating in the mixer, while simultaneously the swellable material, e.g. guar gum, is added.

The fixation of rapidly swellable materials with an aqueous binder suspension or solution is not trivial, because in contact with water the swellable materials tend to rapidly swell and disintegrate. Normally, these problems are overcome e.g. by using organic solvents or highly diluted aqueous solutions of the swellable materials. A better possibility is demonstrated in the examples below: New equipments are available which allow to fix the swellable material with an aqueous binder suspension or solution before disintegration of the swellable material takes place. This is mainly due to (a) the high compaction forces caused by the high speed rotation and (b) the high drying capacity of the new equipments. Suitable equipments are e.g.: "Rotoprocessor" (Aeromatic AG, Bubendorf, CH), "Rotogranulator" (Glatt AG, Binzen, FRG), "CF-Granulator" (Freund, Tokyo, Japan).

The following examples are intended to illustrate the invention and are not to be construed as being limitations thereon. Temperatures are given in degrees Centigrade.

EXAMPLE

Sachets containing a dry suspension of multi-layer swellable controlled release pellets with particulary good organoleptic properties for the administration to elderly people and children are obtained - after (a) preparing suitable pellets containing methylxanthines and (b) coating the latter with a layer for controlled release purposes - by (c) overcoating the coated pellets obtained with the swellable material and finally mixing the obtained multilayer pellets with granulated guar gum.

PREPARATION OF MULTI-LAYER SWELLABLE PELLETS (a) Approximately 6 kg pellets, size 0.4–1.0 mm, containing methylxanthines are prepared according to the following formula and process:

A mixture of powders of 1800 g proxyphylline, 1800 g diprophylline, 1200 g anhydrous theophylline, 300 g Prejel ®-PA-5 (pregelatinized slightly oxidized potato starch, supplied by AVEBE, Weendam, Netherlands) and 720 g Avicel ®-PH-105 (microcrystalline cellulose, particle size 20μ, supplied by FMC Corporation, Philadelphia, USA) is prepared in a Diosna mixer for 5 min. The mixture is humidified with a mixture of 180 g silicone emulsion (plasticizer, glidant) in 725 g of water. This mass is kneaded for 1 min and then extruded through a screen with holes size of 0.7 mm diameter (apparatus Fuji Paudal ECDS-60). The extruded mass is spheronized in a marumerizer Q-230 with a speed of 1100 rpm for 2 min, while small quantities, totally≈116 g, of talc (glidant) are added. The pellets obtained are dried for 30 min at 50° in an Aeromatic Strea-7 apparatus. They are sieved, and the fraction between 0.4–1.0 mm size is used for the coating step (b).

(b) 6 kg of the pellets of (a) are coated in a fluidised-bed (Aeromatic SC-2, 10 bar) in a co-current technique with a suspension mixture of 2500 g Eudragit ®-NE-30-D (a 30 % aqueous dispersion of an ethyl acrylate/methyl methacrylate copolymer 70:30, m.w. ~800 000, supplied by Röhm Pharma Darmstadt, FRG) and 500 g of Aquacoat ® ECD-30 [30% aqueous polymeric dispersion of ethyl cellulose having a low particle size (latex form) and a narrow particle size distribution, supplied by FMC Corporation, Philadelphia, USA]. The spray rate of the coating suspension is 45 g/min and the inlet air temperature is 45°. A further solution of 600 g Aquacoat ® ECD-30 is sprayed on and the micropellets are treated in the fluidised-bed for 2 h at 70° and then cooled with air at 22°.

The percentage of release of the total methyl-xanthines in the USP XX paddle method at 50 rpm and 37° C. in the simulated gastric medium is presented in FIG. 1.

(c) 5 kg of the coated pellets of (b) are used to prepare the multi-layer pellets in a "Rotoprocessor" apparatus (Aeromatic AG, Bubendorf, Switzerland). 1.5 kg of guar gum (Meyprogat ®-150, supplied by Meyhall Chem., Kreuzlingen, Switzerland) is fixed on these pellets with the aid of 1230 g binder mixture suspension consisting of 1:1 7 % w/w Klucel ®-LF (hydroxypropylcellulose supplied by Hercules Inc., Wilmington, USA) in water with Eudragit ® NE-30-D. The rotation speed of this apparatus is 425 rpm and the spray rate onto the pellets is 21 g/min with a powder incorporation rate of 20 g/min. The temperature of the inlet air is 35° and the volume of air flow 100 m³/h. Simultaneous rotating and drying is performed for 10 min at 60° and 760 m³/h, before a suspension mixture consisting of 125 g Aquacoat ®-ECD-30, 12.5g Pharmacoat ®-603 (hydroxypropylmethylcellulose, supplied by Shinetsu Chemical Co., Tokyo, Japan), 25 g of talc and 125 g of water is sprayed on with a spray rate of 20 g/min. The multi-layer swellable pellets are obtained after sieving and collecting the fraction of size having 0.4–1.25 mm diameter.

The percentage of release of total methyl-xanthines is presented in FIG. 1.

PREPARATION OF GUAR GUM GRANULES

Granules of guar gum are obtained by granulation of a mixture consisting of 212 g guar gum (Meyprogat ®-150), 235 g sorbitol powder and a solution of 2.5 g saccharine sodium (sweetener) in 200 g water. Spray granulation is used with the co-current technique, with a spray rate of 7 g/min and an inlet air temperature of 40°. The granules obtained are dried for 30 h at 75° and then calibrated through a sieve with openings of 1.0 mm size.

PREPARATION OF SACHETS

A dry suspension which can be filled into sachets is obtained after mixing 179 g of multi-layer swellable pellets with 90 g of granulated guar gum and 10 g of orange flower for 20 min.

The percentage of release of total methyl-xanthines from reconstituted suspension in water - tested with the USP dissolution paddle method at 50 rpm and 37° C. - is presented in FIG. 1.

I claim:

1. Pellets comprising
   (a) a core, containing microparticles of at least one pharmaceutically active substance,
   (b) optionally one or more coating layer(s) and
   (c) an outer layer which rapidly swells and rapidly becomes jellified in contact with water containing a rapidly swelling and rapidly jellifying material selected from the group consisting of xanthan gum and derivatives thereof, guar gum and derivatives thereof, alginates, polysaccharides, cellulose derivatives, polyvinyl alcohol, pregelatinized starches and swellable acrylic polymers,
   which pellets, when contacted with water, are rapidly dispersed so as to generate a viscous, homogeneous suspension that can easily be swallowed.

2. Pellets according to claim 1, characterized in that the size of the microparticles used in the core (a) is 0.2–3.0 mm.

3. Pellets according to claim 1, characterized in that the size of the microparticles used in the core (a) is 0.3–1.5 mm.

4. Pellets according to claim 1, characterized in that the size of the microparticles used in the core (a) is 0.6–1.2 mm.

5. Pellets according to claim 1, characterized in that the pharmaceutically active substance incorporated into the core (a) is a member of the group consisting of drugs for the treatment of hypokaliaemia, psychotherapy drugs, non-steroidal antiinflammatory drugs, drugs for the therapy of hypocalcemic states or for calcium supplementation, drugs for the treatment of osteoporosis, muscle relaxants, antihistaminica, bronchodilators, drugs for the treatment of venous diseases, antitussive drugs, antipyretics, vitamines, cardiovascular and vascular drugs, geriatric drugs, pediatric drugs, drugs useful to balance the hydroelectrolytes, antibiotic drugs, nootropica, anthelmintica and histamin $H_2$ receptor antagonists.

6. Pellets according to claim 1, characterized in that they contain one or more coating layer(s) (b).

7. Pellets according to claim 1, characterized in that they contain one coating layer (b).

8. Pellets according to claim 1, characterized in that the swellable material used in the swellable outer layer (c) is guar gum.

9. Pellets according to claim 1, characterized in that the swellable material used in the swellable outer layer (c) is hydroxypropylmethylcellulose.

10. A pharmaceutical preparation for oral administration comprising pellets according to claim 1.

11. A pharmaceutical preparation according to claim 10, characterized in that it is a dry suspension.

12. A dry suspension according to claim 11, characterized in that it in addition comprises granules of a swellable material.

13. A sachet containing a pharmaceutical preparation of claim 11.

14. A sachet containing a pharmaceutical preparation of claim 12.

* * * * *